United States Patent [19]
Joseph et al.

[11] Patent Number: 5,150,607
[45] Date of Patent: Sep. 29, 1992

[54] SPINNING DROP TENSIOEXTENSIOMETER

[75] Inventors: Daniel D. Joseph, 1920 S. First St., Apt. 2302, Minneapolis, Minn. 55454; Dave A. Hultman, Anoka, Minn.

[73] Assignee: Daniel D. Joseph, Minneapolis, Minn.

[21] Appl. No.: 742,291

[22] Filed: Aug. 8, 1991

[51] Int. Cl.⁵ .............................. G01N 13/02
[52] U.S. Cl. ................................. 73/64.48
[58] Field of Search .................... 73/53, 64.4

[56] References Cited

U.S. PATENT DOCUMENTS

| | | | |
|---|---|---|---|
| 4,250,741 | 2/1981 | Scriver, II et al. | 73/64.4 |
| 4,523,456 | 6/1985 | Baird et al. | 73/64.4 |
| 4,644,782 | 2/1987 | Joseph | 73/64.4 |

OTHER PUBLICATIONS

Article entitled "Measurement of Interfacial and Surface Tensions in Polymer Systems" by Patterson et al., *J. Polymer Sci.: Part C, No. 34*, pp. 31–43 (1971).
Article from *Polymer Engineering and Science*, Mar. 1986, vol. 26, No. 6, "Measuring of Interfacial Tensions of Molten Polymer Systems by Means of the Spinning Drop Method", by J. J. Elmendrop and G. De Vos, pp. 415–417.

*Primary Examiner*—Hezron E. Williams
*Assistant Examiner*—Michael Brock
*Attorney, Agent, or Firm*—Kinney & Lange

[57] ABSTRACT

A spinning drop tensioextensiometer provides for the ability to rotate a tube carrying two different polymers, under conditions which keeps the polymers melted, and which causes the less dense polymer to form a drop of a generally cigar shape. By measuring the diameter of the drop at desired angular velocities upper and lower bounds for interfacial tension can be determined. Further, these bounds define relaxation curves for the extensional relaxation of a blend of two polymers. The polymers are placed in a glass tube that is rotated at high speed within an oven that has an opening through which the diameter of the inner polymer drop can be measured utilizing optical equipment, such as a video camera projecting an image onto a monitor.

19 Claims, 6 Drawing Sheets

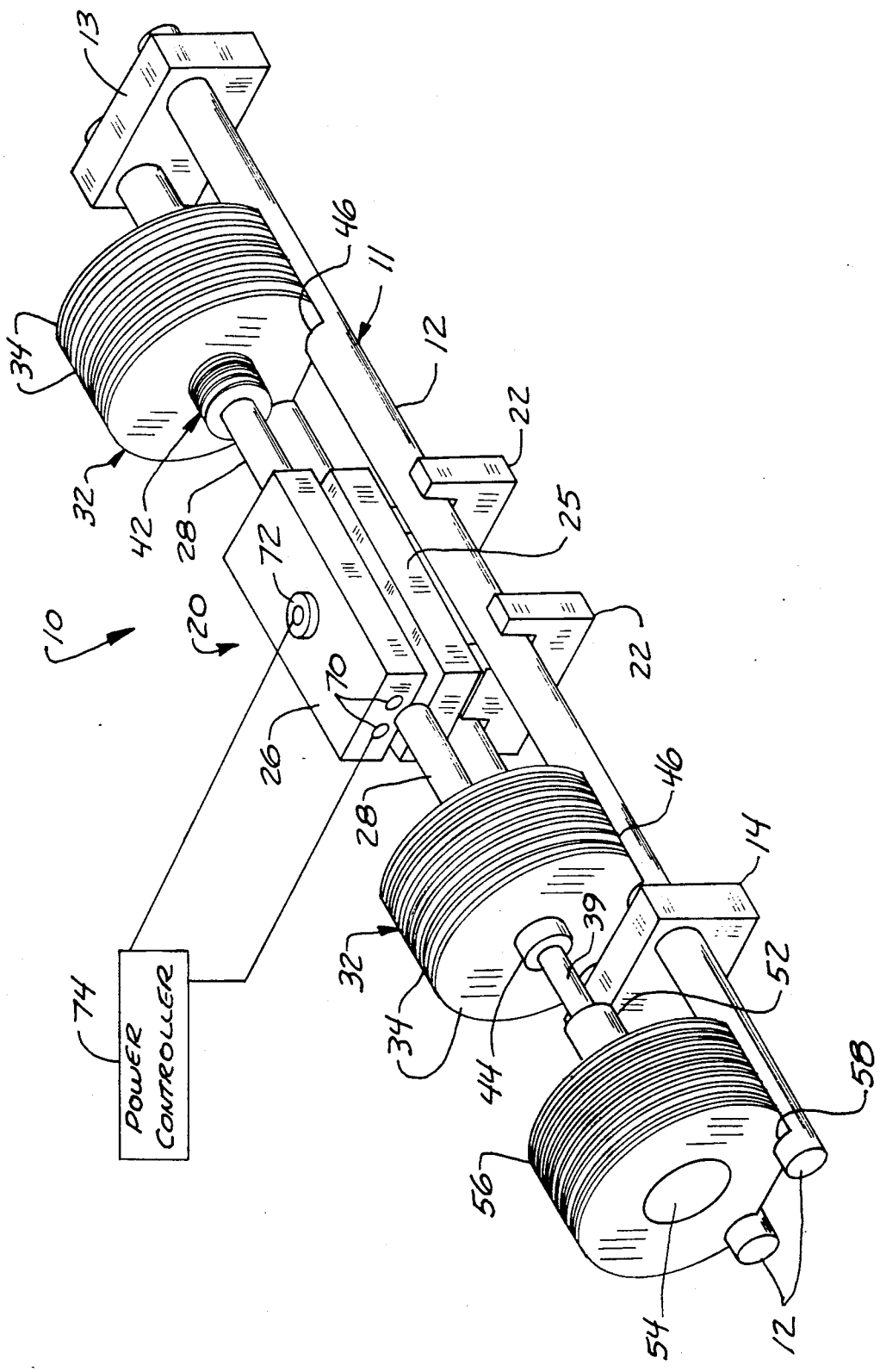

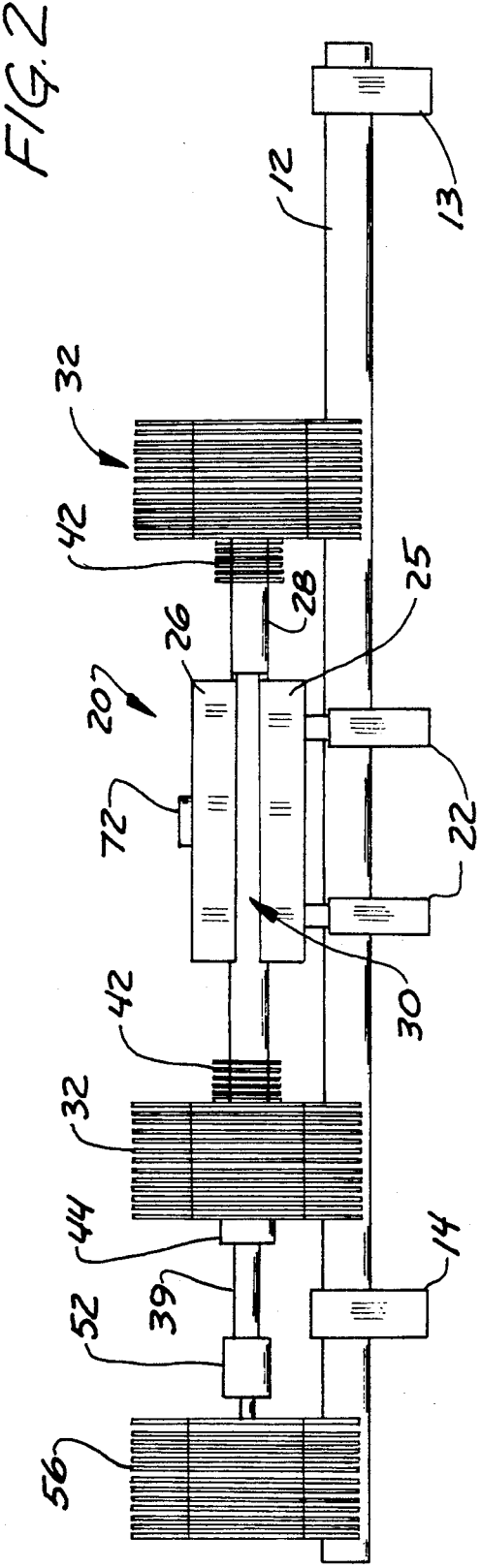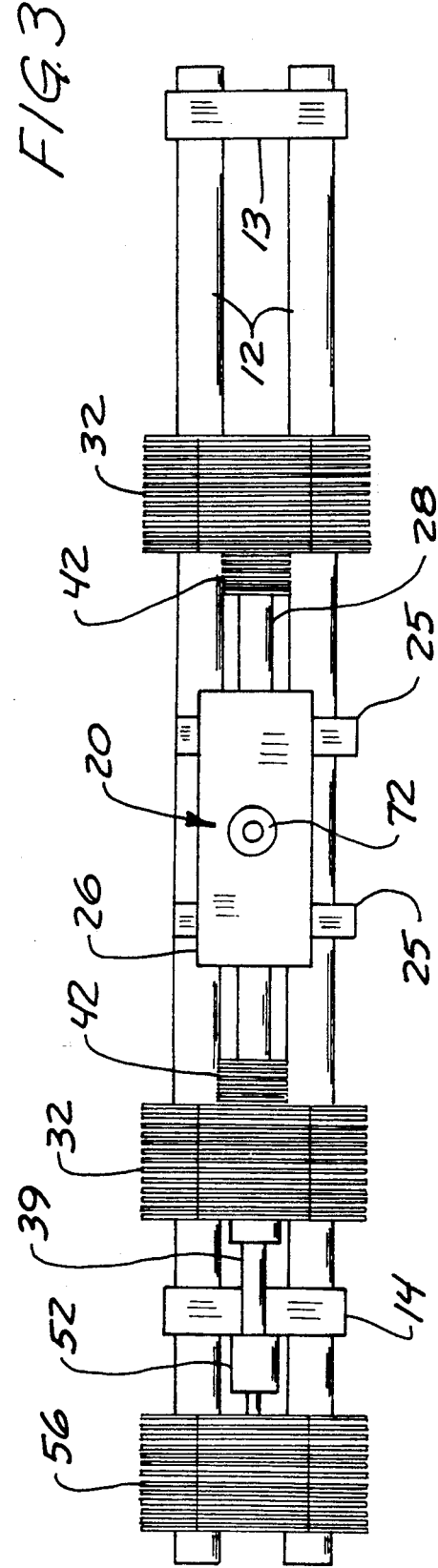

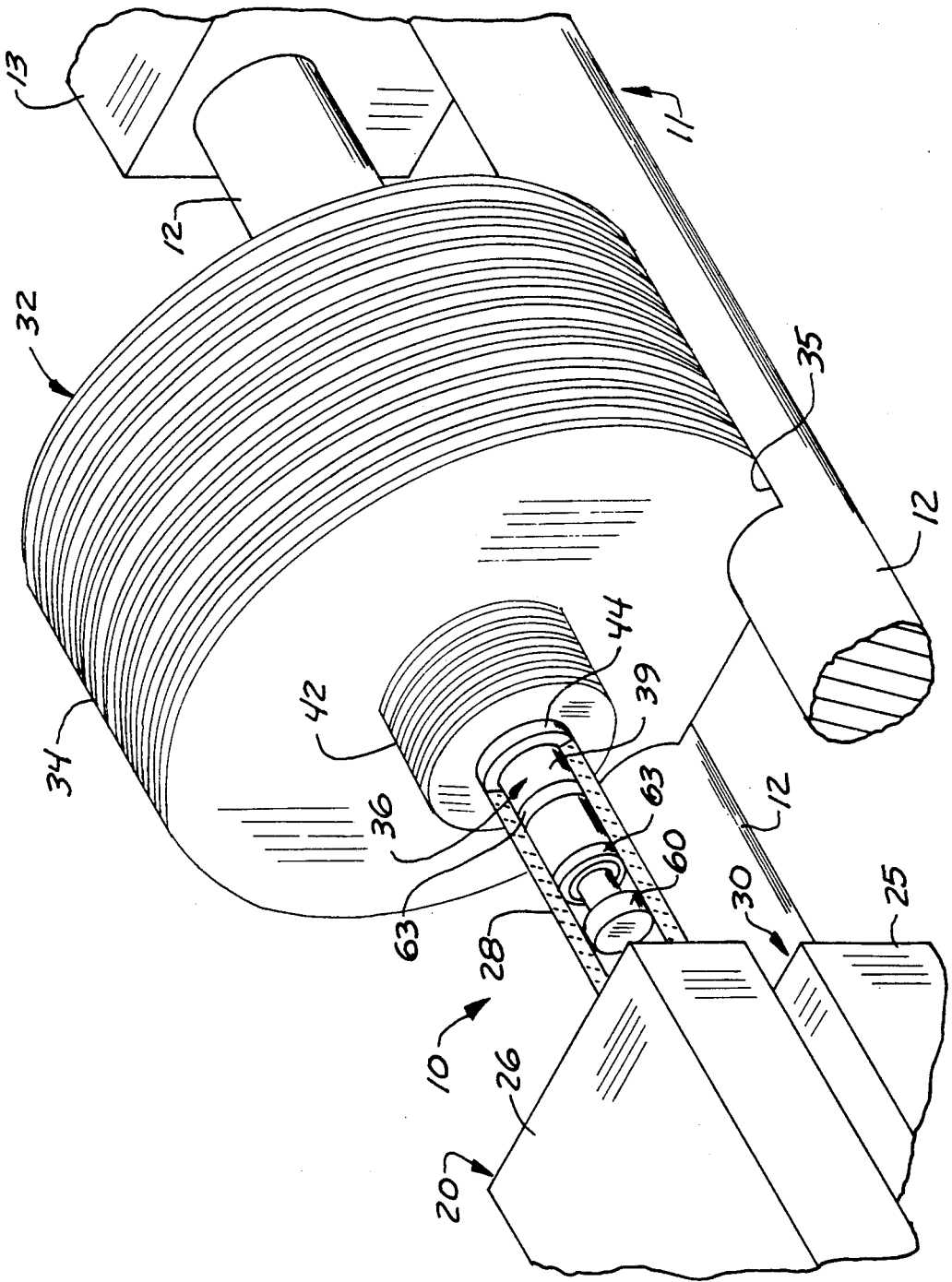

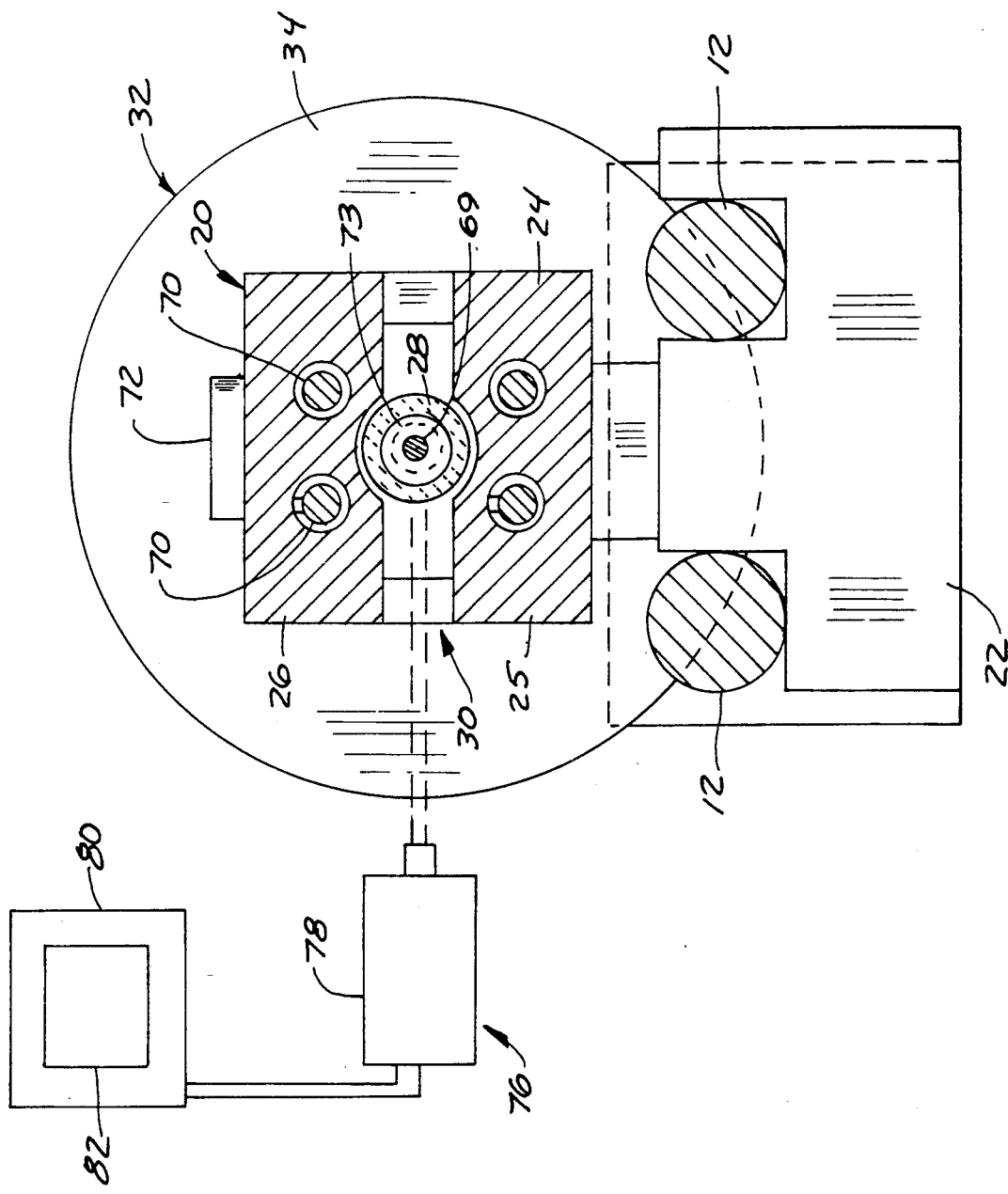

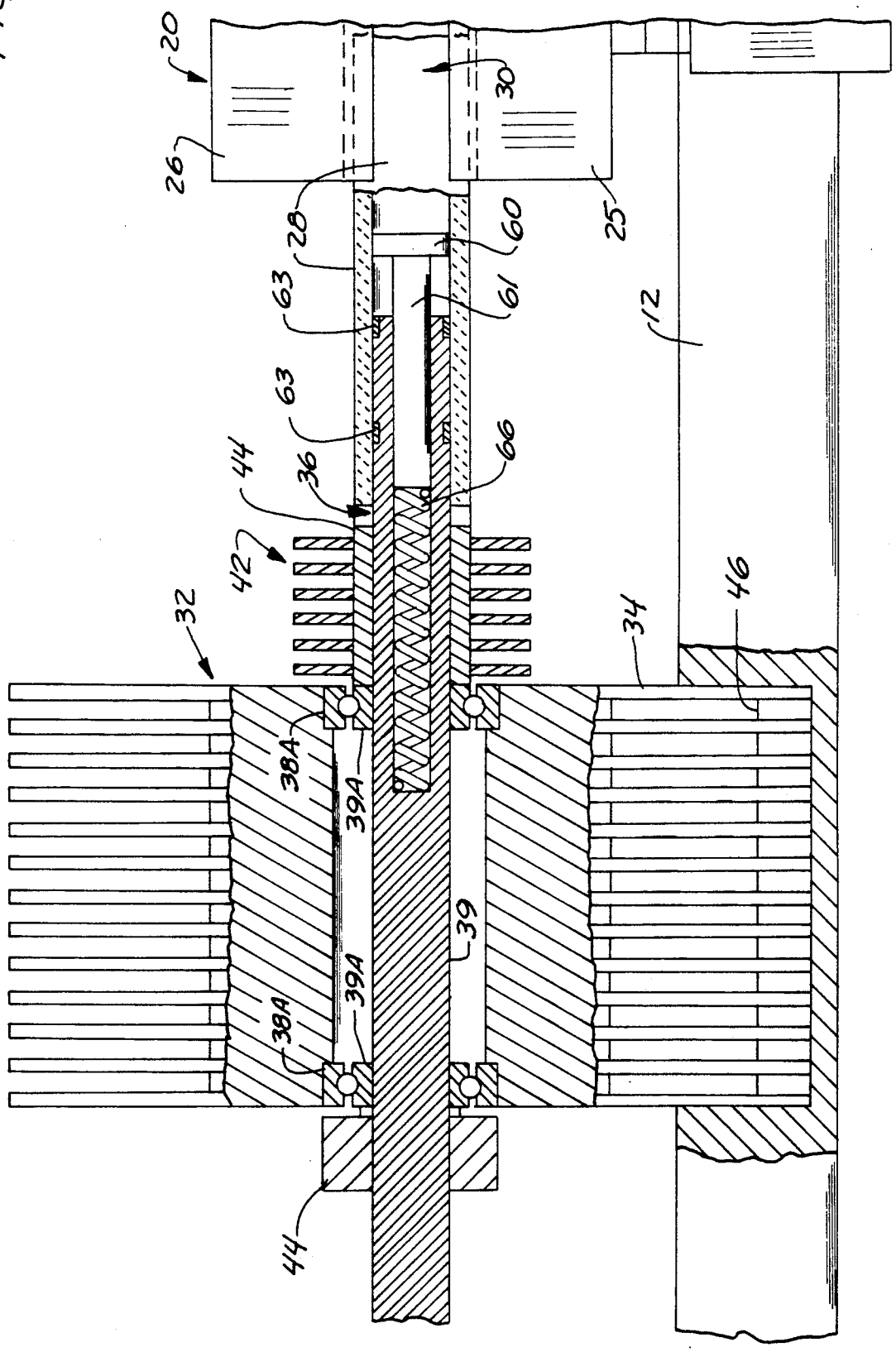

SPINNING DROP TENSIOEXTENSIOMETER

BACKGROUND OF THE INVENTION

The present invention relates to an apparatus for determining the interfacial tension between any two polymer melts, and for determining properties of relaxation in extension of the system comprising the same two polymer melts.

Spinning rod tensiometers have been advanced. U.S. Pat. No. 4644782 discloses a spinning rod interfacial tensiometer utilizing a central rod in a housing. This device works well for certain applications, but when trying to determine the interfacial tension and relaxation time for two polymers, heat must be provided to the system. An adequate opening must also be left for taking measurements of the drop that is formed by the less dense of the polymers. With viscous polymers, the spin-up does not create problems, such as having the less dense polymer thrown to the outside, and because the final speeds are very high, the diameter to be measured can be quite small. The rod in the center of the tube can be used to measure index of refraction, but the rod is not used for measuring the other properties such as interfacial tension and relaxation times for extensional deformation of a blend of two polymers, according to the present invention.

SUMMARY OF THE INVENTION

The present invention relates to a spinning drop tensioextensiometer that is used to measure parameters which provide indication of the relaxation properties and interfacial tension between two different polymer melts of different densities, by rotating hot, two-liquid phase polymers at high speed, and determining the diameter of the inner drop formed by a selected smaller volume of the lighter (less dense) polymer while it is being rotated. Rotation at two different angular velocities establishes upper and lower bounds approaching equilibrium interfacial tension. These bounds are in the form of relaxation curves for the drop which contain information about the response of the blend to extensional deformation. The information is used for determining the properties of pairs of polymer melts and polymer compatibilizers used to prepare polymer blends, such as composite materials having improved strength characteristics.

The instrument permits placing polymers into an elongated tube, closing the ends and providing means for driving the tube about its longitudinal axis while at the same time heating it to temperatures in the range of 300° C. The tube is held very accurately about its center of rotation. The changes in volume of the polymers at different temperatures is accommodated by spring loading an end plunger of the tube to provide for volume change upon expansion or contraction of the polymers.

The tube is placed within a heater or furnace that provides the necessary temperature for melting while also providing an opening or slit that permits measuring the diameter of the internal drop of the less dense polymer on a real time basis to determine when a substantially equilibrium condition is reached under different angular velocities.

As shown, a video camera of known design is used to monitor the drop, and is used in combination with a calibrated display to provide for real time diameter measurements.

The diameter of the inner drop is the control information needed for determining interfacial tension, as well as tension-relaxation functions. Compensating data can be obtained as to the effect of different mixes of polymers or the effect of the addition of surfactants or other additives on the polymer properties.

BRIEF DESCRIPTION OF THE DRAWINGS

FIG. 1 is a perspective view of a spinning drop tensioextensiometer made according to the present invention;

FIG. 2 is a side elevational view of the device of FIG. 1;

FIG. 3 is a top plan view of the device of FIG. 1;

FIG. 4 is an enlarged perspective view of one end bearing assembly used with the present invention, with parts in section and parts broken away;

FIG. 5 is a sectional view taken as on line 5—5 in FIG. 2;

FIG. 6 is an enlarged sectional view of the tube support used in a typical assembly for testing polymers;

DETAILED DESCRIPTION OF THE PREFERRED EMBODIMENTS

Figure 7:
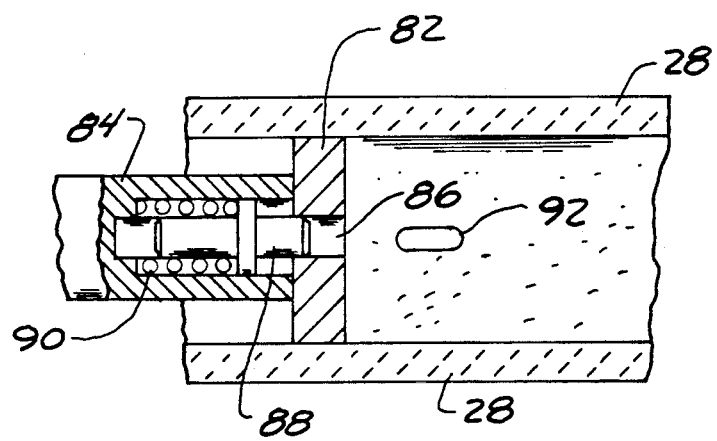
FIG. 7 is a schematic fragmentary sectional view of a modified end plug used for controlling internal pressures in the tube.

Referring to the drawings, a spinning drop tensioextensiometer made according to the present invention is illustrated generally at 10, and comprises a support frame 11 that includes precision guide rods 12,12 which are spaced apart and supported on suitable end supports 13 and 14 that hold the support rods 12,12 relative to a support surface.

A central furnace 20 is supported on suitable blocks 22, and is located generally in the center portions of the rods 12,12. The blocks 22 extend up between the rods 12 to support the lower half 25 of the furnace 20. The upper half of the furnace indicated at 26 is also supported suitably on the lower half 25 of the furnace and can be suitably supported so it can be removed or opened.

An elongated glass tube 28 is used for containing both of the polymers to be tested, and extends longitudinally along a central rotational axis passing through the furnace. It can be seen that the upper portion and lower portions of the furnace 20 leave a gap 30 that permits visual examination of the glass tube 28 when the tube is held in position. The furnace portions are recessed in the center portions to provide for clearance with the cylindrical outer surface of the glass tube 28 as it spins on its axis.

The tube 28 in turn is supported for rotation with end adapters on suitable bearing assemblies including an idler end bearing assembly 32, which is supported in a multifinned heat dissipating radiator 34 made up of a plurality of spaced discs or fins. The radiator 34 is supported in suitable notches 35 on the rods 12,12. The bearing assembly 32 supports the glass tube 28 for rotation about the longitudinal axis of the tube 28 through the use of end plugs 36, that fit inside the glass tube 28 and serve to seal it as well as supporting it on rotating bearings that are housed in the support 34.

The glass tube 28 is also supported in bearings and the arrangement is the same as at the assembly 32. The end plugs 36 each comprise a shaft 39 with an outer end that extends out of the end of the tube 28 and mounted in bearings 38 that are supported on bearing supports 32 and radiator 34. The support 32 at the drive end is supported in notches 46 on the rods 12.

As shown in FIG. 6, the bearing outer housings 38 are in heat conducting relationship to the fins. An inner bearing race 39A supports the shaft of plug 36. On the drive end, a suitable coupling 52 couples shaft 39 so that it in turn is driven from an electric motor 54. Heat radiating discs or fins 56 surround the motor and are in heat transfer relation thereto. The outer edges of fins 56 are supported in notches 58 formed near the outer end of the rods 12.

The motor 54 can either be a high speed motor or else geared up through a suitable gear box to obtain a rotational speed for the shaft 39 and the glass tube 28 in the range of 20,000 RPM.

The glass tube 28 is relatively thick (about 2 mm) and is relatively small in diameter (about ½ inch T.D.). It will contain a sufficient amount of the two polymers to be analyzed, as long as the right proportions are added.

As shown, each of the end plugs 36 has a teflon inner end disc 60 supported on a shaft 61. The shaft 61 is telescopically slidably mounted on the interior of shaft 39. The shafts have suitable high temperature O-rings 63 on the outer surfaces thereof which will grip and seal on interior surface of glass tube 28. The teflon disc 60 will first slide in the tube to contact the solid polymers and then expand as the tube 28 heats up and the polymers melt to tightly seal against the interior of the glass tube and prevent substantial heat from being conducted to the respective shafts 39. The shaft 39 of each of the end support plugs 36 has an interior bore that mounts the shaft 61 carrying end disc 60, and suitable springs 66 are provided on the interior of this bore to urge the teflon seal disc 60 inwardly. The discs 60 are at opposite ends of the glass tube 28, and place some spring load against the polymers that are within the tube. Additional cooling for the bearings 38 is provided by a set of cooling fins 42 that are fixed on a sleeve, which fits over shaft 38 at each bearing mount. A shaft collar 44 is provided for axially locating the shaft properly.

The O-rings 63 provide for a rotational drive coupling as well as seals. The respective shafts 38 for end plugs 36 are mounted into the bearings 38. The drive shaft 39 at the drive end of the tube 28 is longer than the shaft 38 at the idler end and is coupled through the coupling 52 so that end plug can be rotated by the motor 54, which in turn rotates the glass tube 28.

Figure 8:
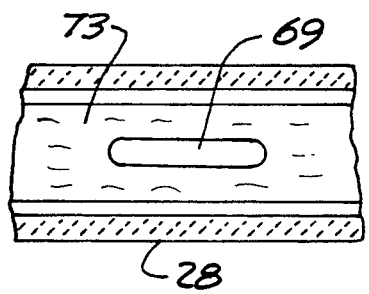
FIG. 8 is a schematic representation of illustrating the effect of a method of preparing polymers and subsequent heating and rotating such polymers in a tube according to the present invention.

The glass tube 28 is loaded with either a machined cylinder of polymers, or with pellets of the solid polymers. When pellets are used, there are voids between pellets which contain air and which can be a problem. A new method of overcoming the problem of voids is to fill tube 28 with glycerin or another heavy liquid which does not mix with the polymers and is liquid at room temperatures, to fill up the voids after adding the pellets. Glycerin is heavier than the more dense polymer and when the tube is heated and rotated, the glycerin moves to the outside in a layer 73 as shown in FIG. 8. Merely melting the polymer pellets is not feasible because of the large amounts of air in the voids. The glycerin filling overcomes problems with void volumes.

The glycerin acts as a dense polymer and forms a layer around the outside of both polymers and since it is liquid at room temperatures, it fills the void volume and eliminates the need for precisely machining the polymers as solid blocks that slide tightly into the tube 28.

The tube 28 is mounted with both of the end plugs 36 in place after the polymers are inserted, and the teflon discs 60 bear against the polymer and glycerin. The bearing supports are mounting the shafts 38 and can be separated from rods 12 and then put into place with tube 28. The upper portion 26 of the furnace will have been removed for placing the tube 28 and the bearing supports on the frame. The upper portion 26 will then be replaced so that it covers the glass tube 28. The heaters indicated generally at 70 within the furnace portions 24 and 26 are connected to a suitable power source that can be controlled with a thermocouple 72.

The polymers are then heated up, at the same time that the motor 54 is running so that the glass tube 28 and the polymers are being spun as they melt. To aid in keeping the bearings and supports cool a blower is used to blow cooling air across the fins. Ducts can be used for directing the cooling air to the desired regions. There is substantially less volume of the lighter polymer than of the more dense polymer. The lighter polymer will form a drop in the center of the heavier or more dense polymer as the tube spins. The glycerin forms a layer at the outside. The readings of the diameter of the interior drop can be commenced as soon as the melting has occurred, and the heat will continue to keep the polymers liquid (highly viscous) under control of the thermocouple 72. As the polymers are spun, the polymer drop 69 in the center of the tube 28 will eventually start to elongate, much like a cigar (see FIG. 8). The length must be more than four times the diameter for reliable readings. The diameter measurements will be taken with instrumentation indicated generally at 76 (FIG. 5) which comprises a video camera 78 and a monitor 80. The monitor screen has suitable calibrations 82 thereon so that the image projected of the interior polymer drop which is indicated at 69 in FIG. 5, will be monitored as it decreases in diameter and elongates during the spinning. The heavier or more dense polymer is shown at 73 outside of the interior drop 69 in FIG. 5 as well. Readings will be taken until the interior drop diameter tends to reach a stable value at a first selected rotational or angular velocity. When a bounding or leveling off of the diameter is reached with time at a first velocity, the angular velocity will be changed (usually lowered) and the drop 69 will reform. The diameter will again move toward a boundary level at a different diameter from the first diameter because of the different angular velocity. Readings of the drop diameter are taken during this time as well, and the results are used to determine interfacial tension values substantially as that shown in FIG. 9, which is a plot of interfacial tension curves of two heavy materials, glycerin and STP, (which simulate melted polymers) based on time at two velocities to provide the values above and below equilibrium interfacial tension.

Figure 9:
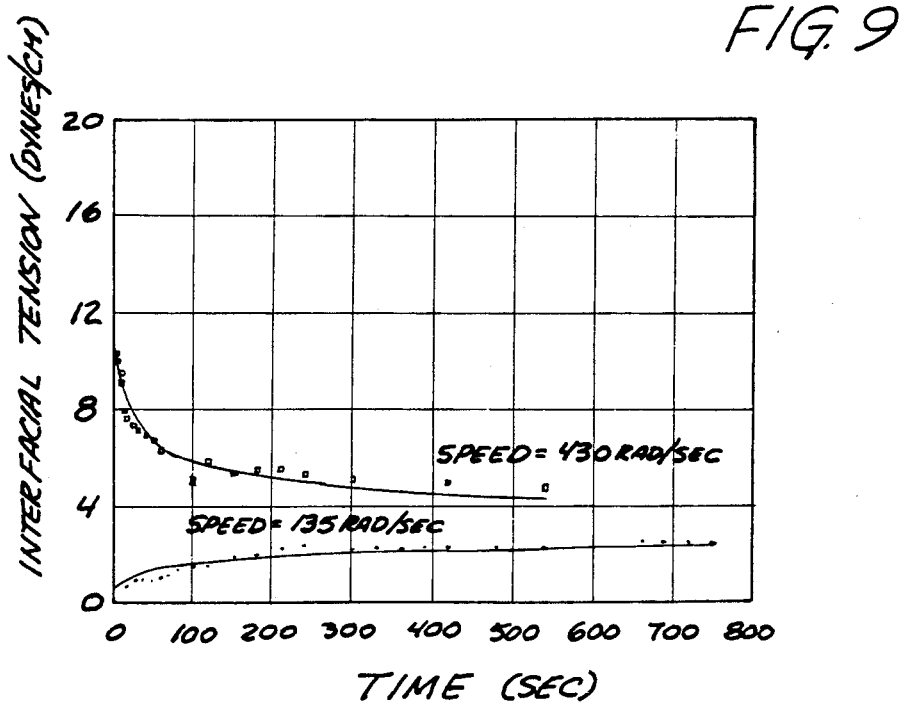
FIG. 9 is a plot representative of a typical interfacial tension bounding determination between two polymers.

FIG. 9 shows the results of operation of the present device to snow the relaxation characteristics of the polymer drop that is on the interior of the more dense polymer.

The variation of the density $\rho$ with temperature of the two polymers can be measured by using the present device. The volumes and weights of the two polymers can be determined by measuring the volume of the polymer drop and of the heavier polymer and weighing them, respectively. The refractive index (n) also is determined by known means. The diameter of the rotating drop (d) is measured as disclosed. The value of the equilibrium interfacial tension $T_e$ is obtained from the formula:

$$T_e = \frac{(\rho_1 - \rho_2)\Omega^2 d^3}{32n^3}$$

Omega ($\Omega$) is the speed of rotation of the drop. The speed must be large enough so that the drop has spread into a cylinder with its axis is on the center line of rotation, and with a length greater than four times the diameter (d). $\rho_1$ is the density of the heavier polymer and $\rho_2$ is the lighter polymer. The known spinning drop method of measuring interfacial tension does not work well for polymer melts, because the polymers are too viscous for the system to come to equilibrium in a time shorter than several hours. The degradation of a polymer held at high temperatures for a long time is significant, so the results from the prior devices are inaccurate.

The present device utilizes a new method of upper and lower bounding of interfacial tension using overspin and underspin, that is, speeds that are quite high wherein a curve is formed as shown in the upper portions of FIG. 9, and then dropping the speed substantially and forming another curve that approaches equilibrium as shown in the lower plot or curve in FIG. 9. The selection is made so an overly large initial diameter is obtained, and then an overly small initial diameter is obtained. The curves show determination of the equilibrium interfacial tension by use of the method of overspin and underspin for Glycerol/STP. It can be deduced that 2.5 dyn/cm$\leq T_e \leq$4 dyn/cm from the underspin and overspin relaxation functions shown.

The variation of the diameter of the rotating drop with time, d(t), may be used to determine the characteristic response times of the system of two polymer melts. It is, therefore, presented in the following formula:

$$T(t) = \frac{(\rho_1 - \rho_2)\Omega^2 d(t)^3}{32n^3}$$

This is the transient interfacial tension, and such that:

$$T(\infty) = T_e$$

This is independent of the speed of rotation, and in the present system, T(t) is called the tension relaxation function.

The relaxation times of the composite of the two polymers is dependent on the relaxation time of each one of them, the two viscosities, the two densities, the interfacial tension, and the angular velocity of the rotation. The properties of relaxation of polymers have been explored previously, and the information provided by the present invention provides data that will aid in using the polymers in various blends.

When solid cylinders of polymers are used to load the tensioextensiometer, they have to be machined to be quite close in size to the tube, and then inserted. The solid cylinders contain dissolved air which comes out when the polymers are heated, and if the sample is also rotated at the same time, the pressure is lower in the center of the sample and the air bubbles will appear in the center.

In order to deal with the dissolved air, the structure shown in FIG. 7 is utilized, and comprises using a small spring-loaded piston which actually could go into the end disc 60 of the end plugs, and the spring can be placed into the shaft of the plunger shown at 61. Thus, a schematic showing in FIG. 9 would use a slightly larger shaft 61, and a suitable disc 82 would be used inside the tube 28, and would slidably fit therein, and would have a main support shaft 84 that would be similar to the shaft 61. The interior of this piston of the disc 60 could have a small bore 86 therein in which a piston member 88 is mounted. The piston member is backed with a spring 90 and slides inside a suitable bore in the shaft 84 that holds the disc 82 in place. It should be noted that the disc 82 does not necessarily have to be spring loaded in this instance, because the machine cylinders can be cut to precise lengths. When the polymer melts and an air bubble indicated at 92 is formed, the internal pressure will be increased as the air bubble causes the polymer to expand into the opening 86, as shown in FIG. 7. The spring 90 will resist this movement, and the pressure will be maintained high enough to keep the air in solution with the polymer, rather than forming air bubbles. The spring 90 thus must be sufficient to compress the bubble 92 to prevent its formation, and keep it dissolved so that it will not affect readings or operation of the unit.

The unique arrangement of heaters and rotational drive provide an accurate and low cost way of analyzing the relaxation functions and interfacial tension of two polymers.

The present invention comprises a spinning drop device which allows measuring curves of relaxation of two polymers which yield bounds on the equilibrium surface tension from above and below the equilibrium level. The relaxation curves are important in the study of the effects of surfactants on polymers. Another application is to study effects of compatibilizers used to make polymer blends. The device can also be used for studying stabilization of emulsions of crude oil in water. The relaxation curve contains important rheological information related to the extensional viscosity of the two liquids. The desired information can be extracted from the measured curves of relaxation.

The improvements in the apparatus relate to the need to have carefully controlled measurements of the radius of a long spinning drop as it evolves from one equilibrium configuration to another after a step change of the angular velocity. The measurement systems, using the video camera, can be aided with laser optics. High resolution cameras with frame averaging capabilities are available and useful. A video microscope with time readout also can be used so the drop radius measurement can be made as a function of time. Image enhancement software to enhance the drop boundary can be used, and a high resolution video monitor currently available is preferred.

Although the present invention has been described with reference to preferred embodiments, workers skilled in the art will recognize that changes may be made in form and detail without departing from the spirit and scope of the invention.

What is claimed is:

1. An apparatus for determining properties related to the relaxation function of polymers of two different densities comprising:

a tubular member defining an internal chamber, and removable means for sealing at least one end of the tubular member;

means for supporting said tubular member for rotation about a longitudinal axis of the tubular member, said means for supporting including precision bearings for rotationally supporting the tubular member at locations spaced from the ends of the tubular member;

heat dissipating means in heat transfer relationship with said precision bearings for conducting heat away from the bearings;

a furnace member mounted on the apparatus and supported adjacent to substantial portions of said tubular member to provide heat to the contents of said tubular member; and the furnace having an opening through which the tubular member can be observed for measuring diameters of a quantity of less dense polymer formed into a drop on the interior of said tubular member.

2. The apparatus as specified in claim 1 wherein said tubular member is a transparent cylinder.

3. The apparatus as specified in claim 2 including means for spinning the tubular member at velocities which cause the less dense polymer to elongate and reduce in diameter in the center of the tubular member, and means for measuring the changes in diameter through the opening in the furnace while the tubular member is spinning.

4. The apparatus as specified in claim 1 wherein said means to support comprise plug means which fit inside the tubular member on at least one end thereof, said plug means including a spring load portion for compressing and permitting expansion of materials between other portions of the plug means and an opposite end of the tubular member.

5. The apparatus as specified in claim 4 wherein said spring load portion comprises a spring loaded plug which fits snugly inside the tubular member and will slide axially along the tubular member as material in the tubular member expands and contracts under temperature changes.

6. The apparatus as specified in claim 5 wherein said plug adjacent the polymer material retained within the tubular member comprises a low friction material that expands when the temperature is at a maximum to seal against an interior surface of the tubular member.

7. The apparatus as specified in claim 4 wherein said tubular member is a glass tube and the means to support on the one end further includes a steel plug positioned outwardly from said first mentioned plug within the tubular member sized to provide contact with the cylinder when the temperature is raised to the desired level for melting the two polymers.

8. The method of preparing samples of two polymers of different densities for heating and analysis while placed in a spinning tube comprising the steps of:

closing at least one end of the tube and filling the tube with desired quantities of the polymers in the form of solid pieces;

filling the tube to a desired level with a dense liquid that fills interstitial spaces between the pieces of the polymers within the tube;

closing the tube, and simultaneously heating and spinning the tube about a longitudinal tube axis to melt the polymers, the dense liquid forming a layer between the tube exterior and the melted polymers.

9. The method of claim 8 including the step of providing a liquid which does not mix with said polymers, and is liquid at room temperature for filling the tube to said desired level.

10. The method of claim 8 including the step of providing glycerin as the dense liquid.

11. The method of claim 8 including the analysis steps of spinning the tube at a velocity to cause a drop of a less dense polymer to form near the axis of the tube and measuring a diametric dimension of the drop of the less dense polymer across a span of time to determine rheological properties of the polymers.

12. A method of investigating rheological properties of two polymers comprising the steps of placing two polymers having different densities in a tube, the less dense of the polymers having a smaller volume than the other, heating the polymers in the tube to melt the polymers, spinning the tube at a first rotational velocity about a central axis to form an elongated drop of the less dense polymer, measuring the diameter of said elongated drop as a function of time until the diameter of the elongated drop stabilizes at a value near the diameter of equilibrium interfacial tension, changing the speed of rotation of the tube to cause a change in physical dimensions of said elongated drop, and measuring the changes in diameter of the elongated drop with respect to time at the second angular velocity until the diameter stabilizes at a value near the diameter of equilibrium interfacial tension, the velocities being selected to establish upper and lower bounds relative to equilibrium interfacial tension to determine tension relaxation functions of the polymers.

13. A method of establishing upper and lower bounds of a tension relaxation function for two polymers of different densities comprising the steps of:

placing the polymers into a transparent tube capable of withstanding heat sufficient to melt the polymers, and heating the polymers at the same time that the tube is spun at a first angular velocity about a substantially horizontal axis;

measuring the diameter of a formed drop of the less dense polymer as a function of time until the diameter substantially stabilizes;

changing the angular velocity of the tube such that the diameter of the less dense polymer drop changes significantly;

measuring the diameter of the drop as a function of time until the diameter stabilizes, to thereby establish bounds of a tension relaxation function for the polymers.

14. The method of claim 13 wherein the angular velocities are selected so that the tension relaxation functions based upon interfacial tension calculations are from both above and below the equilibrium interfacial tension value.

15. The method of claim 13 wherein both the first and second angular velocities are sufficiently high so that the drop of less dense polymer attains a length that is greater than four times its diameter.

16. An apparatus for determining properties related to the relaxation function of polymers of two different densities comprising:

a tubular member defining an internal chamber for holding polymers;

means for supporting said tubular member for rotation about a longitudinal axis of the tubular member, said means for supporting including removable plug means which fits inside the tubular member on at least one end thereof and seals the tube end, said plug means including a spring load portion for compressing relative to other portions of the plug means and for permitting expansion of materials between the plug means and an opposite end of the tubular member;

means for rotationally driving the tubular member about its longitudinal axis; and a furnace member mounted on the apparatus and supported adjacent to portions of said tubular member to provide heat to melt polymers contained in said tubular member, the furnace having an opening through which the tubular member can be observed for measuring diameters of a quantity of less dense polymer formed into a drop on the interior of said tubular member.

17. The apparatus as specified in claim 16 wherein said spring load portion comprises a spring loaded plug which fits snugly inside the tubular member and will slide axially along the tubular member as material in the tubular member expands and contracts under temperature changes.

18. The apparatus as specified in claim 16 wherein said plug adjacent the polymer material retained within the tubular member comprises a low friction material that expands when the temperature rises to seal against an interior surface of the tubular member.

19. The apparatus of claim 16 wherein said means to support comprises bearings spaced from respective ends of the tubular member and heat dissipating means associated with the bearings for conducting heat from the bearings.

* * * * *